United States Patent
Jespersen et al.

(10) Patent No.: US 8,708,957 B2
(45) Date of Patent: Apr. 29, 2014

(54) ELECTRONICALLY MONITORED INJECTION DEVICE

(75) Inventors: Søren Kragh Jespersen, Sørup (DK); Claus Urup Gjødesen, Copenhagen (DK); Andre Larsen, Dragør (DK)

(73) Assignee: Novo Nordisk A/S, Bagsvaerd (DK)

( * ) Notice: Subject to any disclaimer, the term of this patent is extended or adjusted under 35 U.S.C. 154(b) by 78 days.

(21) Appl. No.: 12/811,169

(22) PCT Filed: Dec. 31, 2008

(86) PCT No.: PCT/EP2008/068389
§ 371 (c)(1),
(2), (4) Date: Oct. 1, 2010

(87) PCT Pub. No.: WO2009/083600
PCT Pub. Date: Jul. 9, 2009

(65) Prior Publication Data
US 2011/0009821 A1    Jan. 13, 2011

Related U.S. Application Data

(60) Provisional application No. 61/019,902, filed on Jan. 9, 2008.

(30) Foreign Application Priority Data

Dec. 31, 2007 (EP) .................................. 07124175

(51) Int. Cl.
*A61M 5/20* (2006.01)
*A61M 37/00* (2006.01)

(52) U.S. Cl.
USPC ............................. 604/135; 604/131; 604/157

(58) Field of Classification Search
USPC ...................... 604/131, 187, 136, 65–67, 157
See application file for complete search history.

(56) References Cited

U.S. PATENT DOCUMENTS

| 3,944,843 A | 3/1976 | Vaz Martins |
| 4,515,584 A | 5/1985 | Abe et al. |

(Continued)

FOREIGN PATENT DOCUMENTS

| CA | 2359375 | 7/2000 |
| DE | 3236374 | 4/1984 |

(Continued)

OTHER PUBLICATIONS

Beckmann, Sensors, Memory, Circuits, Polyapply Newsletter, vol. 1(3) (2006).

(Continued)

*Primary Examiner* — Laura Bouchelle
*Assistant Examiner* — Rebecca E Eisenberg
(74) *Attorney, Agent, or Firm* — Wesley A. Nicolas; Marc A. Began; Reza Green (57) ABSTRACT

The present invention relates to a medical injection device (1) for use in combination with a medicament filled cartridge (2), the injection device being provided with a spring-assisted injecting mechanism where energy released from the spring moves a plunger (3) of a held cartridge (2). Sensor circuitry is adapted to detect speed related data during injection so at to detect an abnormal speed condition, such as a needle blocking condition, a priming condition or an air purge condition. The invention also relates to a medical injection device comprising sensor circuitry and user communicating means to provide a recommended needle retraction waiting period which is dependent on the speed of injection.

9 Claims, 2 Drawing Sheets

(56) References Cited

U.S. PATENT DOCUMENTS

| | | |
|---|---|---|
| 4,634,431 A | 1/1987 | Whitney et al. |
| 4,812,724 A | 3/1989 | Langer et al. |
| 4,838,860 A | 6/1989 | Groshong et al. |
| 4,871,351 A | 10/1989 | Feingold |
| 4,898,578 A | 2/1990 | Rubalcaba |
| 4,950,246 A | 8/1990 | Muller |
| 5,135,485 A | 8/1992 | Cohen et al. |
| 5,163,904 A | 11/1992 | Lampropoulos et al. |
| 5,221,268 A | 6/1993 | Barton et al. |
| 5,320,609 A | 6/1994 | Haber et al. |
| 5,536,249 A | 7/1996 | Castellano et al. |
| 5,593,390 A | 1/1997 | Castellano et al. |
| 5,628,309 A | 5/1997 | Brown |
| 5,662,612 A | 9/1997 | Niehoff |
| 5,681,285 A | 10/1997 | Ford et al. |
| 5,720,733 A | 2/1998 | Brown |
| 5,728,074 A | 3/1998 | Castellano et al. |
| 5,741,211 A | 4/1998 | Renirie et al. |
| 5,820,602 A | 10/1998 | Kovelman et al. |
| 5,879,360 A | 3/1999 | Crankshaw |
| 5,879,630 A | 3/1999 | Lescouzeres et al. |
| 5,928,201 A | 7/1999 | Poulsen et al. |
| 5,933,671 A | 8/1999 | Stephany et al. |
| 5,971,963 A | 10/1999 | Choi |
| 5,989,221 A | 11/1999 | Hjertman |
| 5,998,989 A | 12/1999 | Lohberg |
| 6,019,745 A | 2/2000 | Gray |
| 6,110,148 A | 8/2000 | Brown et al. |
| 6,161,364 A | 12/2000 | Kolberg |
| 6,268,722 B1 | 7/2001 | Kogure et al. |
| 6,340,357 B1 | 1/2002 | Poulsen et al. |
| 6,391,005 B1 | 5/2002 | Lum et al. |
| 6,547,755 B1 | 4/2003 | Lippe et al. |
| 6,585,698 B1 | 7/2003 | Packman et al. |
| 6,673,033 B1 | 1/2004 | Sciulli et al. |
| 6,966,895 B2 | 11/2005 | Tribe |
| 7,080,936 B1 | 7/2006 | Simpson |
| 7,195,609 B2 | 3/2007 | Huegli |
| 2002/0002326 A1 | 1/2002 | Causey, III et al. |
| 2002/0020654 A1 | 2/2002 | Eilersen |
| 2003/0009133 A1 | 1/2003 | Ramey |
| 2003/0073954 A1 | 4/2003 | Moberg et al. |
| 2003/0114800 A1 | 6/2003 | Veasey et al. |
| 2003/0216663 A1 | 11/2003 | Jersey-Willuhn et al. |
| 2003/0233075 A1 | 12/2003 | Huegli |
| 2004/0010204 A1 | 1/2004 | Weber et al. |
| 2004/0024361 A1 | 2/2004 | Fago |
| 2004/0051368 A1 | 3/2004 | Caputo et al. |
| 2004/0158304 A1 | 8/2004 | Cory et al. |
| 2004/0171983 A1 | 9/2004 | Sparks et al. |
| 2004/0207385 A1 | 10/2004 | Gafner et al. |
| 2004/0230157 A1 | 11/2004 | Perry et al. |
| 2004/0267207 A1 | 12/2004 | Veasey et al. |
| 2005/0171476 A1* | 8/2005 | Judson et al. .............. 604/131 |
| 2006/0173439 A1 | 8/2006 | Thorne et al. |

FOREIGN PATENT DOCUMENTS

| | | |
|---|---|---|
| DE | 3923079 | 1/1991 |
| DE | 19503230 | 8/1996 |
| DE | 10201875 | 5/2003 |
| DE | 102004046003 | 3/2006 |
| DK | 200100240 | 2/2001 |
| DK | 2005/00116 | 6/2005 |
| EP | 017318 | 10/1980 |
| EP | 338806 | 10/1989 |
| EP | 387854 | 9/1990 |
| EP | 422482 | 4/1991 |
| EP | 454331 | 10/1991 |
| EP | 615762 | 9/1994 |
| EP | 1074273 | 2/2001 |
| EP | 1095668 | 5/2001 |
| EP | 1557163 | 7/2005 |
| EP | 1557189 | 7/2005 |
| EP | 1723977 | 11/2006 |
| EP | 1728529 | 12/2006 |
| EP | 1782853 | 5/2007 |
| EP | 2000161 | 12/2008 |
| FR | 2622457 | 5/1989 |
| FR | 2740345 | 4/1997 |
| GB | 2153445 | 8/1985 |
| GB | 2229497 | 9/1990 |
| GB | 2309644 | 8/1997 |
| IN | 165367 | 3/1986 |
| JP | 56-163486 | 12/1981 |
| JP | 01-100495 | 4/1989 |
| JP | 02-126184 | 5/1990 |
| JP | 02-182267 | 7/1990 |
| JP | 7-502678 | 3/1995 |
| JP | 09166474 | 6/1997 |
| JP | 3017167 | 11/1999 |
| JP | 2002-511776 A | 4/2002 |
| JP | 2004-313383 A | 11/2004 |
| JP | 2006250582 | 9/2006 |
| JP | 2007-530860 A | 11/2007 |
| JP | 2010-511414 A | 4/2010 |
| WO | WO 85/02256 | 5/1985 |
| WO | WO90/09202 | 8/1990 |
| WO | WO93/01573 | 1/1993 |
| WO | WO95/24233 | 9/1995 |
| WO | WO97/30742 | 8/1997 |
| WO | WO97/33638 | 9/1997 |
| WO | WO99/07425 | 2/1999 |
| WO | WO99/15214 | 4/1999 |
| WO | WO99/65548 | 12/1999 |
| WO | WO0037129 | 6/2000 |
| WO | WO01/26710 | 4/2001 |
| WO | WO02/05876 | 1/2002 |
| WO | WO0224257 | 3/2002 |
| WO | WO02/053214 | 7/2002 |
| WO | WO02/064196 | 8/2002 |
| WO | WO02092153 | 11/2002 |
| WO | WO03/057283 | 7/2003 |
| WO | WO03/063680 | 8/2003 |
| WO | WO03/099357 | 12/2003 |
| WO | WO2004/028598 | 4/2004 |
| WO | WO2004/080306 | 9/2004 |
| WO | WO2004/084795 | 10/2004 |
| WO | WO2004/095379 | 11/2004 |
| WO | WO2005/089835 | 9/2005 |
| WO | WO2006/039930 | 4/2006 |
| WO | WO2006/045425 | 5/2006 |
| WO | WO2006/045525 | 5/2006 |
| WO | WO2006/045529 | 5/2006 |
| WO | WO2006/069454 | 7/2006 |
| WO | WO2006/076921 | 7/2006 |
| WO | 2006/084821 A2 | 8/2006 |
| WO | 2006/113521 A2 | 10/2006 |
| WO | WO2006/116997 | 11/2006 |
| WO | WO2006/128794 | 12/2006 |
| WO | WO2007/030957 | 3/2007 |
| WO | WO2007/041843 | 4/2007 |
| WO | 2007/092637 A2 | 8/2007 |
| WO | WO2007/107558 | 9/2007 |
| WO | WO2007/107561 | 9/2007 |
| WO | WO2007/134954 | 11/2007 |
| WO | WO2008/037801 | 4/2008 |
| WO | WO2008057223 | 5/2008 |
| WO | 2009039203 A2 | 3/2009 |

OTHER PUBLICATIONS

Trankler, Hans-Rolf, R. Oldenbourg, Verlag, Munchen, Wien.
English Abstract of DE10201875.
English Abstract of DE102004046003.
English Abstract of DE19503230.
English Abstract of DE3923079.
English Abstract of DE3236374.
English Abstract of EP387854.
English Abstract of EP422482.
English Abstract of FR2622457.
English Abstract of FR2740345.
English Abstract of IN165367.

(56) References Cited

OTHER PUBLICATIONS

Machine Translation of JP09166474.
English Abstract of JP2006250582.
English Abstract of JP02-126184.
English Abstract of JP56-163486.
English Abstract of JP3017167.
English Abstract of JP01-100495.
English Abstract of JP02-182267.
Common Insulin Injection Challenges: http://www.bd.com/us/diabetes/page.aspx?cat=7001&id=7265.
Gnanalingham, M.G. et al., Accuracy and Reproducibility of Low Dose Insulin Administration Using Pen-Injectors and Syringes, Downloaded From ADC.BMJ.com on Jan. 9, 2008.
Annersten, M. et al., Insulin Pens Dribble From the Tip of the Needle After Injection, Practical Diabetes Int., vol. 17(4), pp. 109-111 (2000).
Office Action in U.S. Appl. No. 09/137,014, filed Aug. 20, 1998; Inventors: Jensen et al., of Jul. 9, 1999.
Office Action in U.S. Appl. No. 09/137,014, filed Aug. 20, 1998; Inventors: Jensen et al., of Feb. 18, 2000.
Office Action in U.S. Appl. No. 10/076,025, filed Feb. 13, 2002; Inventors: Larsen et al., of Nov. 28, 2003.
Office Action in U.S. Appl. No. 10/076,025, filed Feb. 13, 2002; Inventors: Larsen et al., of Nov. 15, 2004.
Office Action in U.S. Appl. No. 12/293,247, filed Sep. 16, 2008; Inventor: Andre Larsen, of Nov. 25, 2009.
Final Action in U.S. Appl. No. 12/293,247, filed Sep. 16, 2008; Inventor: Andre Larsen, of Jun. 7, 2010.
Opposition in Related European Patent Application EP 02711784.5 of Sep. 19, 2008.
Search Report Issued in Connection With European Appln No. 06005602.5, Mailed Oct. 16, 2006.
Search Report Issued in Connection With PCT Appln. No. PCT/EP2007/052630, Mailed Nov. 12, 2007.

\* cited by examiner

ELECTRONICALLY MONITORED INJECTION DEVICE

CROSS-REFERENCE TO RELATED APPLICATIONS

This application is a 35 U.S.C. §371 national stage application of International Patent Application PCT/EP2008/068389 (published as WO 2009/083600), filed Dec. 31, 2008, which claimed priority of European Patent Application 07124175.6, filed Dec. 31, 2007; this application further claims priority under 35 U.S.C. §119 of U.S. Provisional Application 61/019,902 filed Jan. 9, 2008.

The present invention relates to medical injection devices for injecting metered doses of a medicament. More specifically, the invention relates to medical injection devices having means for precisely monitoring dose delivery and means for notifying or alerting a user of the correct or incorrect use of the injection device.

The invention enables a more efficient use of injection devices while offering improvements with respect to dose delivery accuracy.

BACKGROUND OF THE INVENTION

In the disclosure of the present invention reference is mostly made to the treatment of diabetes by injection or infusion of insulin, however, this is only a preferred use of the present invention.

In order to permit a patient to administer a proper dose, various mechanical injection devices have been proposed which offer additional electric circuitry for measuring and displaying the size of a dose which will be administered during an injection procedure. Examples of such devices are shown in WO02/064196 and in WO02/092153.

Some mechanical injection devices are equipped with an energy accumulating member such as a spring for the purpose of accumulating mechanical energy during a pre-injection procedure, e.g. by straining a spring during a dose setting procedure, to enable the accumulated energy to drive a drive member during the subsequent injection procedure so as to expel a fixed or an individually set dose. WO2008/037801 disclose such devices wherein additional electric circuitry is provided for detecting the amount of a set dose or the amount of an injected dose.

Several different unwanted conditions is likely to occur during operation of mechanical injection devices, such as the occurrence of a blocked injection needle or the patients usage of an injection device which has not been properly primed or purged prior to making an injection. Such conditions may present serious hazards if they are not acknowledged by the user and appropriate action is taken. In mechanical injection devices where the user exerts a force upon the drive mechanism for forcing the plunger of the cartridge forward during the complete injection procedure, the user may experience some perceptive feedback from the drive mechanism during operation thereof. Generally, such feedback provide some degree of alertness as to eventual unwanted conditions. However, when using spring assisted injection devices, such as the ones shown in WO2008/037801, the mechanical perceptive feedback may be rather limited.

The documents US 2003/0009133, US 2003/0073954, U.S. Pat. No. 6,340,357, WO 03/099357 and WO2006/116997 all relate to motorized injection or infusion apparatuses where motor driving circuitry is used for controlling the motor drive. The motor driving circuitry can be easily adapted to monitor the drive mechanism during operation to allow for detection of specific conditions and for alerting the patient of the detected condition. In WO 2007/107558 a cartridge sensor system is disclosed, which enables detection of the axial position of a plunger inside the cartridge and by using additional sensors in an associated medication delivery device a needle blockage condition may be detected.

It is desirable following transcutaneous injection of a medicament to wait a short time before withdrawing the needle of the injection device from the skin of the patient. Generally, medical doctors instruct their patients in that they shall, subsequent to carrying out an injection procedure, wait 5-10 seconds, for larger doses even longer, before retracting the needle from the skin. Commonly it is acknowledged that this is necessary because the injected medicament takes a few seconds to disperse locally from the injection site within the body of the patient. If the needle is withdrawn too soon after the medicament has been injected, there is a risk that at least some of the injected medicament may escape through the needle wound and not be dispersed.

Unfortunately, this problem is particularly acute where a patient uses a medicament injection apparatus to self-administer a medicament. A user may become impatient and withdraw the needle before the medicament has dispersed.

In order to alleviate this problem, WO patent application No. 97/30742 discloses an injection device which provides an electronic representation of a recommended waiting period after completion of an injection movement for advising the patient to keep the needle inserted in the skin during the recommended waiting period.

The required waiting period is a time contributing to the overall time needed by a diabetic patient to treat the condition and should generally be minimized. Further, as the waiting period is a passive time (no action needed or allowed by the patient) it is likely to psychologically feel like a larger percentage of the overall time used than the real percentage. Finally, a simple and unintelligent maximum fixed waiting time scheme is likely to increase the risk that some patients become impatient and withdraw the needle prematurely.

To implement the abovementioned principle of recommending a longer waiting period when a large dose has been injected as compared to injection of smaller doses, WO patent application Ser. No. 03/057,283 discloses a medicament injection apparatus where the point in time of actuation of a signal means for signalling the end of the waiting period is made dependent of the amount of the medicament injected. Even though that such a system may be well received by some patients, this simple corrective action may lead to incorrect guidance of the user, having the effect that some users may experience fluid leakage around the needle wound and dripping from the needle when the needle is retracted from the skin.

DISCLOSURE OF THE INVENTION

Having regard to the problems and deficiencies identified above, it is an object of a first aspect of this invention to reduce the risk of imprecise or incorrect dose delivery when delivering a fixed dose or an individually set dose of medication by means of a manually injection device of the spring-assisted type.

Also, it is an object of a second aspect of this invention to improve patient guidance during use of a medical injection device with respect to the correct timing of needle retraction from the skin. A further object is to minimize patient inconvenience while maintaining a high accuracy regarding the amount of medication which is delivered to the patient.

In accordance with the FIRST aspect of the invention, a manual injection device is provided for injecting a medicament from a reservoir of the type comprising a plunger which is driveable towards an expelling end of the reservoir to inject a quantity of medication. The injection device comprises:
- a spring means configured for storing energy during a pre-injection procedure,
- a drive member advanceable to move the plunger of the reservoir towards the expelling end of the reservoir, wherein the drive member is forced during an injection procedure by the spring means when mechanical energy previously stored in said spring means is released
- a dose delivery actuator for triggering release of energy from the spring means,
- a sensor adapted to detect positional information related to the drive member or to a component associated with the drive member, and
- a circuit communicating or coupled with the sensor to process signals sensed by the sensor, wherein the circuit determines speed data from signals sensed by the sensor, compares the speed data with pre-defined speed data and performs a control action if the speed as sensed during injection reaches an abnormal speed condition.

In a preferred embodiment, the invention according to the first aspect provides a device for repetitive injection of individually set doses of a fluid or drug from the reservoir. In alternative embodiments, the device provides for repetitive injections of a fixed dose, wherein the injection device is armed during a pre-injection procedure, to subsequently deliver a fixed dose upon release of the spring means.

The reservoir may be fixedly attached to the remainder of the injection device. Alternatively, the injection device is adapted to receive a medicament reservoir in the form of a replaceable cartridge.

In particular embodiments, the spring means may be provided by a spring, such as a compression spring or a torsion spring. Alternatively, the spring means may incorporate a resilient foam material or a compressible gas medium.

In embodiments where the injection device includes a dose setting mechanism which enables the user to select a particular size of dose to be administered, the spring means may be adapted to be cocked or biased during the dose setting operation. In alternative embodiments, the spring means is adapted to be cocked or biased during an arming operation as referred to above.

The drive member may take form of a piston rod for driving forward the plunger of the reservoir. The said sensor may be coupled to the drive member to sense movements of the drive member during injection. Alternatively, the said sensor may sense movements of other components of the device which is coupled or associates with the drive member, i.e. which moves in synchronism with the drive member at least during injection. In accordance with the particular design of the drive mechanism, the sensor may sense a linear movement or alternatively a rotary movement or still alternatively a helical movement.

The sensor is coupled to the circuit to monitor movements of a component at least during injection, so as to provide positional information relating to the particular component in question. Within the context of this invention, the term "positional information" includes parameters related to the positional data of a component over time as well as parameters related to the velocity of a component over time.

The term "abnormal speed condition" is construed as conditions contrary to normal speed conditions, the normal speed conditions being defined as continuously performed injections where the drive member forces forward the plunger of the reservoir in a continuous movement from the start of the injection to the end-of-dose state, i.e. where the drive member engages the plunger during the entire injection procedure. The end-of-dose state is the state where the drive member is situated after delivery of a complete intended dose.

In some embodiments, the circuit includes signalling means whereby the circuit is adapted to emit a signal as the control action responsive to the detection of an abnormal speed condition. The signalling means may include an electronically controlled indicator such as a display, a light emitter, a speaker for emitting an audible signal, a vibratory unit which produces vibrations or an electro-muscle stimulation (EMS) unit which produce a tactile indication. The circuit may be adapted, responsive to the detection of an abnormal condition, to generate an alarm which is readily acknowledgeable by the user.

Alternatively, or in addition, if the injection device is configured for storing a log comprising data relating to a plurality of administered dose injections, the injection device performs the control action by registering the abnormal situation as an event and stores it along with other data relating to that particular administration, e.g. dose size and time and date of the administered dose, medicament type, BGM data which has been transferred or entered into the device etc. Such information may be shown on a display on the device or it may be communicated to an auxiliary device.

The circuit may include a memory which hold at least one pre-defined threshold speed value. In such setup the circuit is adapted to compare the determined speed data with the at least one threshold speed value to detect the occurrence of an abnormal speed condition.

In one embodiment, the device may be configured to detect a needle blocked condition. In such a system if the speed as sensed during injection is below a first threshold speed, the condition may be deemed to involve an occlusion downstream from the reservoir. In particular, if no movement of the drive member is detected during injection, the speed data as derived from the sensor contains a speed corresponding to no movement of the drive member and this triggers a control action such as an alarm indicating that the needle may be occluded.

The circuit may be adapted to discriminate between an injection where the drive member is in abutment with the plunger and an injection where the drive means do not abut the plunger. It may also be able to detect that the drive member during at least a part of the injection procedure do not abut the plunger. Hence, in such a system, the system may be configured for detecting that the injection device is not properly primed, i.e. that the drive member does not engage the plunger of the reservoir.

The device may be configured to detect a priming condition if the speed as sensed during injection is above a second threshold speed. Alternatively, or in addition, the detection of the priming condition may be detected by analyzing the speed related data set to detect an eventual speed change from the recorded data set, indicating the occurrence of drive member/plunger impact during the injection stroke.

The device may be configured to detect an air purging condition if the speed as sensed during injection is above a third threshold speed and below a fourth threshold speed. Alternatively, or in addition, the detection of the purging condition may be detected by analyzing the speed related data set to detect a speed change from the recorded data set, indicating the occurrence of drive member/plunger impact during the injection stroke.

The above describe speed related data set may be obtained by continuously recording the speed data during injection stroke to obtain a speed profile for the entire injection stroke whereby speed changes can be analyzed.

In particular embodiments, the injection device further include means for measuring the temperature, such as by measuring ambient temperature, the temperature of a particular component of the device or the temperature of the liquid medicament contained in the reservoir. In such embodiments, the speed threshold values may be corrected by taking into account the measure temperature, or the circuit may be adapted to take the temperature measurements into account. For example, the respective threshold values may be lowered if the temperature measurement indicates particular cold operating conditions, while the threshold values may be increased by hot operating conditions. If a temperature of the liquid medicament is to be measured, the reservoir itself may comprise the temperature sensor and the injection device is adapted to communicate/operate the sensor by appropriately wired or wireless connection, such as by using a RFID based temperature sensor associated with the reservoir.

In further embodiments where the device includes a dose setting mechanism, the circuit may be adapted to take the dose size as set into account when analyzing the obtained speed data and comparing the measured data with stored reference data. For instance, for small dose sizes where relative low dosage speeds are predicted, corresponding low speed threshold values may be used.

In some embodiments, the circuit may be configurable to a selected one of a plurality of needle sizes (e.g. needle inner diameter and/or length) so that the threshold speed values change in dependence of the particular choice of needle attached to the injection device.

The injection device may incorporate means for detecting when the dose delivery actuator is actuated. Further the injection device may incorporate means for sensing the end-of-dose state. The circuit may be adapted to monitor the speed data only during time intervals where the dose delivery actuator has been actuated and until the end-of-dose state is detected.

In some embodiments, the injection device incorporate a drive mechanism of a type wherein the dose delivery actuator is operable from a non-active state into an active state in response to a force exerted on the actuator to effectuate the injection movement, wherein the actuator returns to the non-active state when said force is released and wherein that the injection movement is halted when the actuator is returned to the non-active state. In such a device, the monitoring of abnormal speed conditions only takes place when a sensor coupled to the dose delivery actuator senses that the dose delivery actuator is in the active state.

In accordance with the SECOND aspect of the invention, a medical injection device is provided for injecting a medicament from a reservoir of the type comprising a plunger which is driveable towards an expelling end of the reservoir to inject a quantity of medication. The injection device comprises:
  drive means actuatable to drive the plunger of the reservoir towards the expelling end of the reservoir,
  a needle assembly which, in use, releasably connects to the injection device for establishing fluid communication with the reservoir, the needle having a front end insertable into and retractable from the skin of a subject user,
  calculating means for determining a needle retraction waiting period subsequent to completion of an injection operation, and
  user communication means for indicating to the subject user the needle retraction waiting period.
The injection device further comprises speed detecting means adapted to determine a parameter related to the speed of injection. Further, the calculating means is adapted to take into consideration the speed of injection parameter when calculating the needle retraction period.

The convenience of using the above described injection device is improved as the total inuse time is lowered and as passive waiting time is minimized. The potential risk of a user withdrawing the needle prematurely is reduced because the waiting period is limited to what is really needed, and the patient noticing the varying waiting time indications is likely to increase the patient awareness towards the importance of respecting the indicated waiting time.

As used herein, the term "injection operation" is construed to define a movement occurring in the injection device during the injection movement. As such, the injection operation is finalized when the drive means which drives forward the plunger comes to a standstill.

The user communication means may include an electronically controlled indicator such as a display, a light emitter, a speaker for emitting an audible signal, a vibratory unit which produces vibrations or an electro-muscle stimulation (EMS) unit which produce a tactile indication. The user communication means may be adapted to communicate the recommended needle retraction waiting period at the start of the waiting period, during injection and/or at the end of the waiting period. For example, by incorporating a display, a single indication of the particular period in seconds may be displayed at the beginning of the period. Alternatively, a signal is emitted during the waiting period so that the user is able to monitor the progression. Still, alternatively, the user communication means may be adapted to exclusively indicate the instant when the needle can be safely retracted from the skin of the user.

The reservoir to be used with the injection device may be a cartridge prefilled with a medicament. The reservoir may be releasably mounted to the injection device so that the reservoir may be exchanged with a new one when the medicament in the previous reservoir has been exhausted. Alternatively, the reservoir may be fixedly attached to the injection device whereby the reservoir and the injection device is disposed off when the medicament initially contained in the injection device has been exhausted.

The drive means of the injection device may include a drive member such as a rod-shaped or flexible piston rod which is adapted to urge the plunger forward during dose delivery. Further, the drive means may include dose setting means by which the dose size intended to be delivered during the injection operation can be selected by the user. The drive means of the injection device according to the second aspect of the invention may take the form of a manual injection device or alternatively a motorized injection device, such device commonly being designated a "motor-doser".

The injection device may incorporate means for determining an injectable or injected quantity of medication. In that case, the recommended needle retraction waiting period may further be dependent on the quantity of medication injected during the injection procedure or to be dependent on the dose size as set during the dose setting operation.

When the injection device comprises means for determining an injectable or injected quantity of medication, the speed detecting means may be adapted to calculate an average speed of injection based on the injectable/injected quantity and the duration of injection operation.

The drive means may comprise a drive member, such as a piston rod, for engaging the plunger of the reservoir. The speed detecting means may comprise a sensor for sensing movement of the drive member during injection. Alternatively, when the drive means comprises a further component which moves from a first position to a second position when the drive member moves to inject an injectable quantity, the speed detecting means may comprise a sensor for sensing movement of the further component of the drive means during injection.

The speed detecting means may comprise a signal generator which emits pulses during injection movement and a sensor for receiving said pulses, whereby the speed of injection is proportional with the frequency of received pulses during injection. Also the size of an administered dose may be determined by counting the number of pulses received.

The speed detecting means may comprise a processor coupled to a storage wherein a look-up table is stored, said look-up table defining needle retraction waiting period as a function of dose speed and optionally also dose size. After completion of the injection procedure, i.e. when the piston rod comes to a standstill, the controller carries out a query in the look-up table to decide the recommended needle retraction waiting period.

As used herein when referring to the first and second aspect of the invention, the term "manual injection device" defines a non-motorized injection device, i.e. a type of device not incorporating an electric motor and where the energy for carrying out the injection procedure is delivered by the user, such as during the injection operation and/or before the injection operation. Manual injection devices include injection devices where the user actively pushes forward a dosing button throughout the injection procedure as well as injection devices where the user winds a spring-mechanism to accumulate energy during a pre-injecting procedure, such as during dose setting, and where the accumulated energy is used to press forward the drive means of the injection device during the injection procedure.

BRIEF DESCRIPTION OF THE DRAWINGS

In the following the invention will be further described with references to the drawings, wherein FIG. 1a and FIG. 1b shows schematic representations of the effect of varying dosing speed in an injection device.

DESCRIPTION OF EXEMPLARY EMBODIMENTS

Figure 1A:
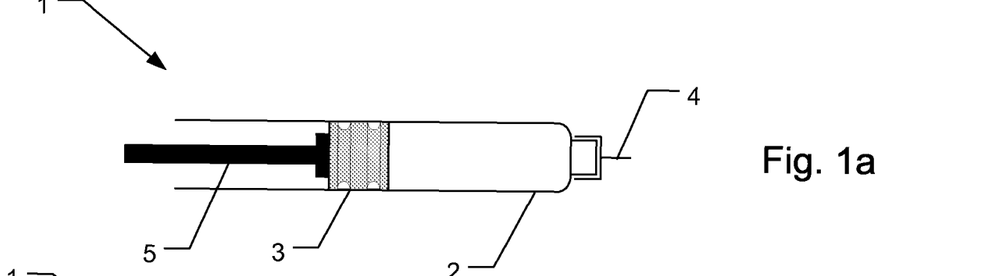
Figure 1B:
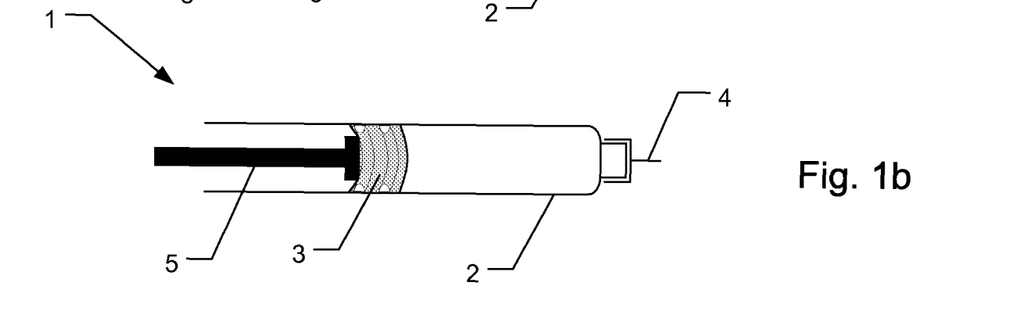

FIGS. 1a and 1b show schematic representations illustrating different states of an injection device 1 for injecting metered amounts of a liquid medication. The injection device holds a medicament filled reservoir in the form of a cartridge 2 and an injection needle 4 which is fixed onto the distal end of the cartridge for establishing fluid communication with the interior of the cartridge. The cartridge 2 accommodates a slideable rubber plunger 3 which is moveable towards the distal end of the device, i.e. towards the right hand side of the figure, by being actuated by a suitable drive mechanism. In the figures, the drive mechanism is schematically illustrated as a piston rod 5 which may be actuated to move towards the distal end of the device to move forward the plunger 3 in the cartridge 2.

The schematic representation shown in FIG. 1a illustrates the effect when a piston rod 5 is actuated by a small force for slowly advancing the rubber plunger 3 in the distal direction towards the needle. As may be seen, during injection, the flexible rubber plunger 3 substantially maintains its un-stressed configuration.

In comparison, a rapid injection movement is schematically depicted in FIG. 1b. When a larger force is exerted on the piston rod 5 the rubber plunger 3 tends to deform and compress due to friction along the wall of the cartridge 2 and due to an increased fluid pressure inside the cartridge. When movement of the piston rod 5 is stopped by halting the drive mechanism, the plunger gradually regains its original shape. During this process, the plunger 3 moves a little further towards the distal end which has the effect of further expelling a small amount of liquid through the needle 4. After sufficient time has elapsed subsequent to completion of the piston rod movement, the plunger 3 has come to a standstill whereby no further liquid is expelled.

As ascertained above, the recommended needle retraction waiting time is to a large extent dependent of the actual expelling procedure which is used during injection. In fact, the above effect may for some injection systems be even more noticeable than the effect observed or hypothesized relating to the risk of backflow of medicament through the needle wound due to time dependent dispersal of medication into the tissue.

According to the second aspect of the present invention, the time lag due to the deformation of the rubber plunger 3 is taken into account by compensating the recommended needle retraction waiting period subsequent to the injection procedure accordingly.

Figure 2:
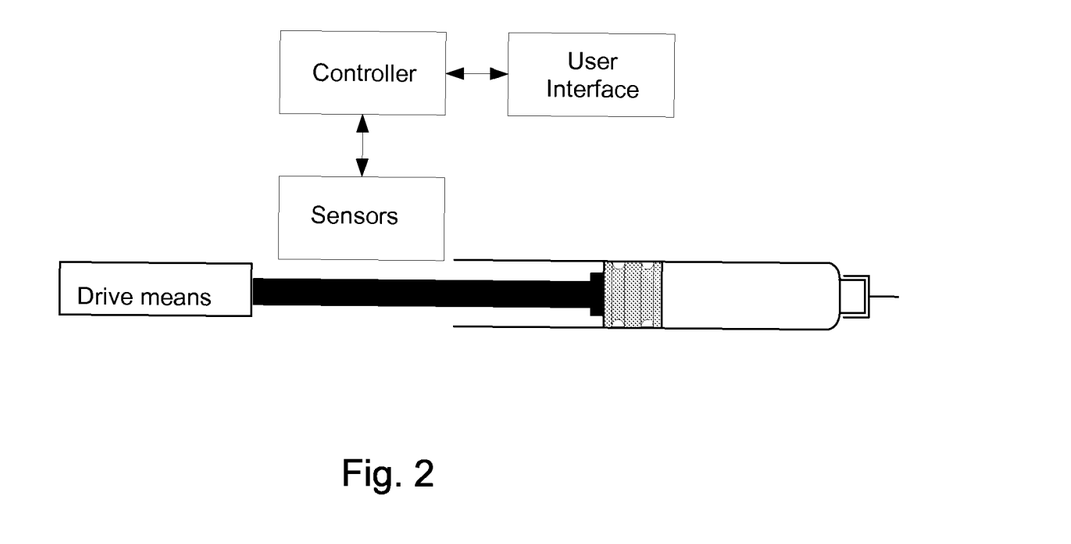
FIG. 2 shows a schematic representation of an injection device according to an embodiment according to the second aspect of the invention.

The schematic representation shown in FIG. 2 depicts an exemplary embodiment according to the second aspect of the invention wherein the injection device 1 is provided with a control system for monitoring various parameters of the device and for controlling a user interface adapted to communicate various operating conditions to the user of the injection device. Furthermore, in order to adjust and inject metered amounts of a medicament, the injection device 1 include drive means which include a dose setting and injection mechanism.

The dose setting and injection mechanism may include a manually driven mechanism where the user provides the energy for moving forward the piston rod by pressing forward an injection button or, alternatively, include a spring assisted injection mechanism where the user, during a dose setting operation, accumulates the required energy in a spring whereby the accumulated energy is released when a subsequent injection is carried out. Still alternatively, the injection mechanism may include a motorized drive mechanism.

The user interface may incorporate one or more of the following: visual indicators such as a display, a speaker for emitting an audible signal such as a simple alarm generated by a tone generator or in the form of synthesized or sampled speech providing instructions to the user, a vibratory unit for generating a vibration signal or an electro-muscle stimulation (EMS) unit generating signals to be sensed by the user.

The control system is coupled to sensor circuitry which is adapted to sense parameters related to the speed of injection of a component of the injection device which component moves during delivery of a dose. The sensor circuitry may include a sensor which is adapted to monitor the dose setting operation and/or the injection operation by monitoring the quantity of medication that is either adjusted during dose setting and/or that is injected during dose delivery. Further sensor circuitry may include timing means which monitors the start time an finish time of dose delivery to thereby derive an average dose speed by which a performed injection has taken place. This further sensor circuitry may include a switch which senses the actuation of the drive mechanism and a switch which senses the end-of-dose condition.

In one simple embodiment, the injection device incorporates a sensor which is adapted to generate pulses during injection as the delivery movements progresses. The number of pulses accumulated during dose delivery correspond to the size of the dose being delivered, whereas the frequency of the detected pulses is proportional to the dose speed during injection.

In other embodiments, the sensor circuitry may include position sensors adapted to monitor specific components of the drive mechanism which move during injection. The position sensors may be either linear sensors or rotary sensors, the particular choice of sensors being selected in accordance with the specific design of the dose setting and injection mechanism. For example, a linear position sensor may be provided that monitors the movements of the piston rod during injection. Alternatively, position sensors are provided which records the movements of a component which moves in synchronism with the piston rod during injection. For example, a component being rotatably mounted in the device and which rotates during injection may be monitored by a rotary position sensor whereby the dosing speed may be calculated from the rotary movement of the rotatably mounted component during injection.

In still other embodiments, the sensor may be of the type which may be adapted to directly provide a signal which is proportional to the speed of movement.

By appropriately sampling the sensor signals during injection, the sensor circuitry can be adapted to continuously monitor the movements of the dose mechanism during injection. Hereby a speed profile may be obtained which is used to estimate a recommended waiting period subsequent to completion of the injection operation for carrying out retraction of the needle from the skin of the user.

As the dose speed to a large extent may vary during expelling of a large dose, particularly when the dose mechanism is a manually driven injection mechanism where the user manually pushes forward an injection button, the needle retraction waiting period may be calculated using the data selected from modified speed data derived from the speed profile recorded during injection. For example, the data relating to speed data from the delivery of doses at the final part of the injection procedure may be given a larger weight than speed data which have been recorded during the initial part of the injection procedure.

Various different algorithms may be incorporated to estimate the correct needle retraction waiting period. In addition, the injection device may incorporate a look-up table wherein combinations of dose speed data, dose size and needle retraction waiting time are stored. After a dosing operation where the relevant data of speed data and dose size have been obtained, a processor of the injection device decides by means of the look-up table the appropriate needle retraction waiting period, and controls the user interface to indicate to the user when the needle may be safely withdrawn from the skin of the user.

In example 1 and 2 as appended to this disclosure, two different methods are described which uses different look-up table configurations in order to estimate a needle retraction waiting period.

Turning now to the first aspect of the invention, a manual injection device is provided which again incorporates a medicament filled cartridge having a slideably mounted plunger which is actuatable by a piston rod for expelling the medicament of the cartridge. The cartridge may be either removeably attached to the injection device or may form an integral (non-replaceable) part of the device. When a new cartridge is to be used, usually the piston rod of the device is situated a distance away from the plunger. In addition, this situation may occur if the user or another person "plays" with the device and thereby accidentally returns the piston rod towards the proximal end of the injection device. If this condition arise, a significant user risk may occur which could lead to an underdose if the risk is not being acknowledged and mitigated.

When the injection device is provided with means for monitoring the dosing speed during the injection procedure, the above situation may be recognized automatically by the following procedure. Reference is again made to FIG. 2 which shows the basic functionality of a suitable manual injection device.

Figure 3A:
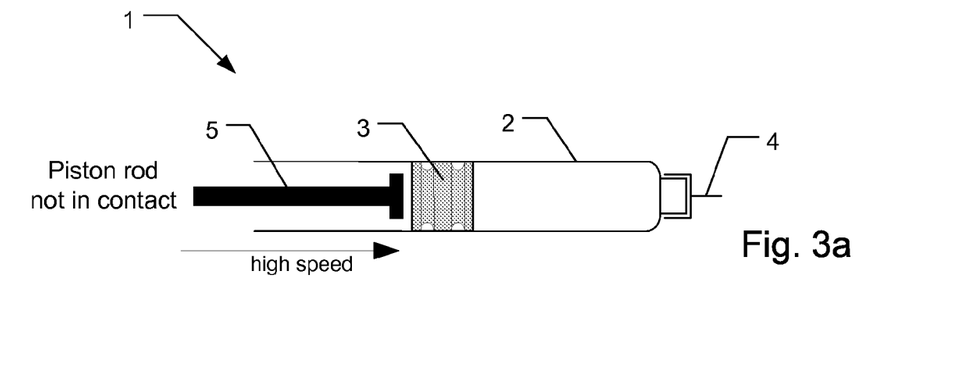
FIGS. 3a and 3b show schematic representations of two conditions of the injection device according to the first aspect of the invention.
Figure 3B:
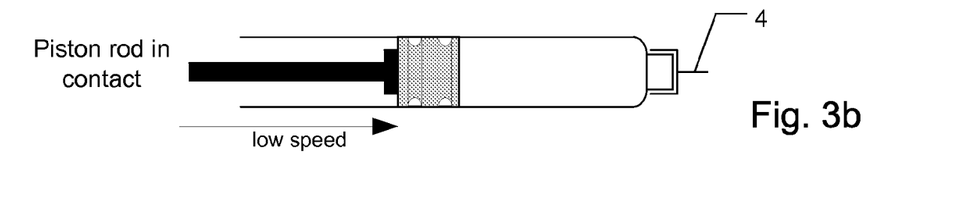

In FIG. 3a, the condition where the piston rod 5 is separated from the plunger 3 of the cartridge 2 is shown. As the force needed for pushing forward the piston rod 5 in the distal direction is significantly lower compared to the situation (as shown in FIG. 3b) where the piston rod 5 abuts the plunger 3, the piston rod tends to move faster than during periods where the piston rod 5 plunges the plunger 3.

By providing sensor circuitry adapted to monitor the movement of the piston rod during dose delivery, or alternatively by monitoring a component which moves in synchronism with the piston rod during injection, the above condition shown in FIG. 3a may be detected by recording the speed profile during injection. Appropriate sensors include position sensors or speed sensors. By suitable configuration of the device, e.g. by programming a processor of the device to analyze the speed profile either concurrent with the injection or after the injection procedure, the above condition may be detected and notified to the user. If a particular speed change is observed during injection, the injection device may be designed to emit an alarm, whereby the user may take appropriate action, such as closely monitoring his or her blood glucose level.

In some embodiments, the injection device may be programmed to analyze the speed profile, so as to determine the travel distance where plunger/piston rod abutment is deemed not to have been established and the travel distance where proper plunger/piston rod abutment is maintained. Accordingly, an estimate of the size of the actual dose expelled may be given and/or an estimate of the dose which lacks from being expelled may be communicated to the user.

A particular simple embodiment may be envisioned when using a spring assisted injection device where the injection of doses occur with a more or less well-defined speed, as defined by the spring actuator. Such device may take the form of an injection device as described in WO2008/037801 which is hereby incorporated by reference. In such a device, sensors are incorporated to enable monitoring movements of the dosing mechanism during dose delivery.

In such an embodiment, a speed threshold may be defined which is associated with the speed profile of a correct injection procedure where medicament is expelled during the entire delivery stroke. Once a particular dose administration is performed, the speed profile of that particular dose administration is recorded. The speed profile is compared with the speed threshold which is then used for discriminating between a correct injection and a non-correct injection. The injection device may hold a plurality of different speed threshold values where each of the threshold values correspond to a respective one of the plurality of possible dose sizes that the injection device is configured to administer. In such an embodiment, the speed profile recorded during administration of a particular dose size is compared with the respective speed threshold for that dose size.

Exemplary typical dose speeds under normal operating conditions using a spring-assisted injector may vary from 4 IU/sec. to 25 IU/sec. using a Novo Nordisk PenFill® cartridge accommodating a 100 U insulin and using a G31×6 mm needle or G30×8 mm needle. When using the spring-assisted injector under lower or higher temperatures, normal injection speeds may be in the range 2 to 30 IU/sec. When injecting small doses such as 1 IU typical dose speeds will be somewhat lower. The above numbers are obtained during a proper injection, i.e. under normal speed conditions.

An exemplary speed threshold value for detecting an air purge condition is 75 IU/sec. An exemplary speed threshold value for detecting a priming condition is 200 IU/sec.

Further embodiments of spring-assisted injection devices may incorporate a more simple sensor setup, which do not necessarily require position sensors or speed sensors for continuously monitoring the delivery stroke. Instead, a dose size sensor for determining doseable quantities or dosed quantities is provided. Timing circuitry is provided which is adapted to measure the time elapsed during the entire delivery stroke. The processor of such an embodiment could be programmed to facilitate a comparison between the measured dose size and its corresponding dose timing with stored reference data.

Reference data may consist of pre-defined values which are referenced by the particular choice of injection needle type and eventually the type of cartridge coupled to the injection device. To take into consideration various different types of needles and cartridges, the injection device may be designed to allow manually setting of the particular choice of needle and cartridge, i.e. by entering a characteristic value of those pre-defined accessories which programs the device accordingly with respect to various dynamic parameters (flow-related parameters, friction related parameters, viscosity of the medicament etc.). Still alternatively, needle and cartridge may be coded so as to enable automatic recognition of the particular choice of needle and/or cartridge by the injection device and to enable automatic programming of the dynamic parameters.

Alternatively, reference data is obtained by recording dose administrations over time with the injection device for a series of injections which by the user is acknowledged as being correct dose administrations. If the timing of a presently administered injection procedure is abnormal as compared to previous correct performed administrations, the device may be configured to provide an indication to the user of this irregularity.

Although the above spring assisted injection devices exert a predictable injection speed owing to the fact that the force/stroke movement is rather well defined and predictable, other manual injection devices having other dosing mechanisms may be used. For example, if the injection device incorporates a drive mechanism where the user delivers the injection force by continuously pressing forward an injection button, a force sensor may be incorporated which continuously measures the force exerted by the user during the injection procedure. By comparing the force exerted with the actual dosing movements, variations in the injection movement attributable to the varying forces exerted by the user may be taken into consideration when analyzing the speed of the movements during injection.

Although only a few exemplary embodiments of the present invention have been described in detail, those skilled in the art will appreciate readily that many modifications are possible in the exemplary embodiments without materially departing from the novel teachings and advantages of the invention. Accordingly, all such modifications are intended to be included within the scope of the present invention as defined in the following claims.

In the above description of the exemplary embodiments, the different structures providing the desired relations between the different components just as the means providing the described functionality for the different components have been described to a degree to which the concept of the present invention will be apparent to the skilled reader. The detailed construction and specification for the different structures are considered the object of a normal design procedure performed by the skilled person along the lines set out in the present specification.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents. This invention includes all modifications and equivalents of the subject matter recited in the claims appended hereto as permitted by applicable law.

Example 1

In this example, the dose speed parameter "v" and the dose size "Vol" which has been delivered during dose delivery are used for calculating a recommended needle retracting waiting period. In this example, the single dose speed parameter v is estimated as an average value derived from the dose speed profile. Also, the size of the dose is taken into account. In the example, U100 insulin (having a concentration of 100 International Units per ml) is accommodated in the cartridge and an injection needle of dimension G31 is connected to the injection device.

The controller of the injection device is provided with a storage having a look-up table pre-loaded into the storage by which combinations of dose sizes and dosing speeds are stored and where appropriate waiting times are stored which correspond to given combinations of dose size and dose speed. For this example, appropriate values of the data in the look-up table can be seen in Table 1.

TABLE 1

| Dose Speed (IU/sec.) | Dose Size (IU) | Waiting time (sec.) |
|---|---|---|
| v < 4 | Vol < 6 | 3 |
| v < 4 | 6 ≤ Vol ≤ 15 | 6 |
| v < 4 | Vol > 15 | 10 |
| 4 ≤ v ≤ 10 | Vol < 6 | 2 |
| 4 ≤ v ≤ 10 | 6 ≤ Vol ≤ 15 | 4 |
| 4 ≤ v ≤ 10 | Vol > 15 | 8 |
| v > 10 | Vol < 6 | 1 |

TABLE 1-continued

| Dose Speed (IU/sec.) | Dose Size (IU) | Waiting time (sec.) |
|---|---|---|
| v > 10 | 6 ≤ Vol ≤ 15 | 2 |
| v > 10 | Vol > 15 | 6 |

After completion of the injection procedure, i.e. when the piston rod comes to a standstill, the controller carries out a query in the look-up table to decide the recommended needle retraction waiting period. After the needle retraction waiting period has elapsed, the injection device signals to the user that the full dose has been properly delivered to the user allowing the needle of the injection device to be safely withdrawn.

Example 2

In this example the needle retraction waiting period is calculated by the controller of the injection device by taking into account the Dose speed parameter "v" and the Dose size "Vol" which has been delivered during dose delivery. Again, the dose speed parameter denotes the average dose speed as calculated after completion of the injection operation.

Figure 4:
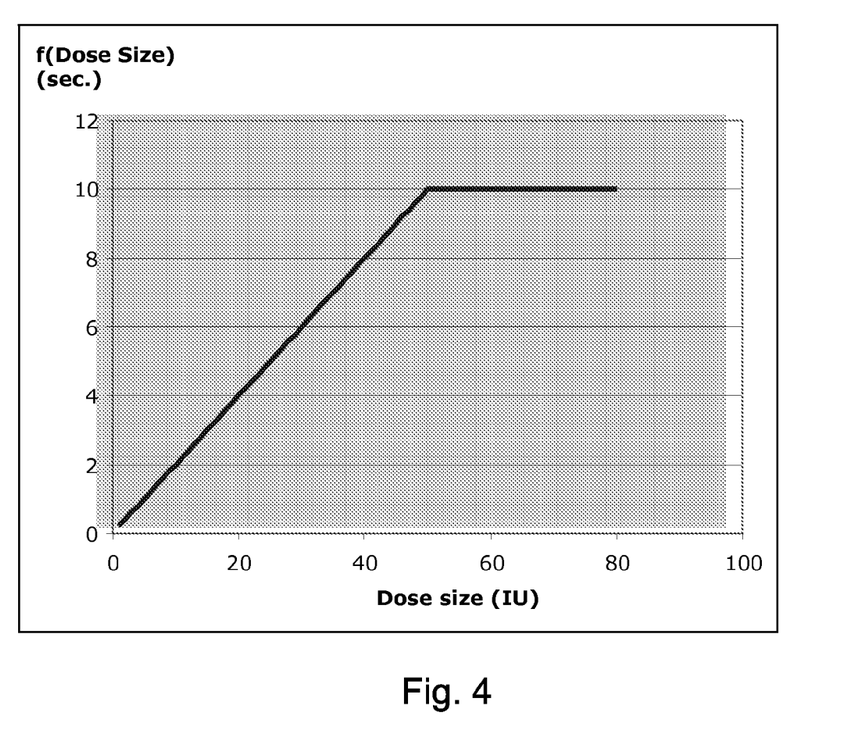
FIG. 4 is a graph showing the functional relationship between dose size and f(dose size) as used in Example 2.

The recommended waiting time which should elapse after the piston rod has come to a standstill but before the needle can be safely retracted can be calculated using the formula waiting time=$f$(Dose size)+$g$(Dose speed)

where f(Dose size) is a time contribution which takes into account the amount being injected and where g(dose speed) is a time contribution which takes into account the dose speed of the dose that has been injected.

f(Dose size) may be defined by the function:

$f$(Dose size)=min (10 s; Vol*0.2 sec./IU)

In FIG. 4, the dose size contribution f(Dose size) is shown as a function of varying dose sizes.

The dose speed contribution g(Dose speed) may be found by using data from a look-up table stored in the injection device, where the look-up table may contain the data shown in Table 2.

TABLE 2

| Dose speed (IU/sec) | g(Dose speed) (sec.) |
|---|---|
| v < 4 | 6 |
| 4 ≤ v ≤ 10 | 4 |
| 10 < v ≤ 20 | 2 |
| v > 20 | 1 |

Again, in this example, after having calculated the recommended needle retraction waiting time on the basis of f(Dose size) and g(Dose speed), the injection device notifies the user of the appropriate moment in time for withdrawing the injection needle from the skin of the user.

The invention claimed is:

1. A medical injection device for use in combination with a medicament filled cartridge, the injection device being a manual injection device not incorporating an electric motor, the injection device being adapted for repetitive injection of individually set or fixed doses of a medicament from a held cartridge, the injection device comprising:
   a dose setting mechanism operable during a dose setting operation for selecting a size of a dose to be administered,
   a spring means configured to accumulate energy during the dose setting operation,
   a drive member advanceable to move a plunger of a held cartridge towards the expelling end of the cartridge, said drive member being forced during injection by the spring means when energy previously stored in said spring means is released,
   a dose delivery actuator for triggering release of energy from the spring means,
   a sensor adapted to detect positional information related to the drive member or to a component associated with the drive member, and
   a circuit communicating with the sensor to process signals sensed by the sensor,
wherein the circuit determines speed data of the drive member from signals sensed by the sensor, compares the speed data with pre-defined speed data and performs a control action if the speed as sensed during injection reaches an abnormal speed condition.

2. The medical injection device as defined in claim 1, wherein the circuit includes signaling means, the circuit being adapted to perform a control action by emitting a signal responsive to a detection of an abnormal speed condition.

3. The medical injection device as defined in claim 1, wherein the circuit includes a memory which hold at least one threshold speed value and wherein the circuit is adapted to compare the determined speed data with the at least one threshold speed value to detect the occurrence of an abnormal speed condition.

4. The medical injection device as defined in claim 3, wherein the at least one threshold speed value comprises a first threshold speed value and wherein the device is configured to detect a needle blocked condition if the speed as sensed during injection is below a first threshold speed value.

5. The medical injection device as defined in claim 3, wherein the at least one threshold speed value comprises a second threshold speed and wherein the device is configured to detect a priming condition if the speed as sensed during injection is above the second threshold speed value.

6. The medical injection device as defined in claim 3, wherein the at least one threshold speed value comprises a third threshold speed value and a fourth threshold speed value and wherein the device is configured to detect an air purging condition if the speed as sensed during injection is above the third threshold speed value and below the fourth threshold speed value.

7. The medical injection device as defined in claim 3, wherein the device further include means for detecting at least one of the ambient temperature, the temperature of a component of the device and the temperature of a cartridge held by the device and wherein the at least one threshold speed value is dependent on the detected temperature.

8. The medical injection device as defined in claim 3, wherein the device include a dose setting mechanism being operable to set a desired dose and wherein the at least one threshold speed value is dependent on the set dose.

9. The medical injection device as defined claim 3, wherein the circuit is configurable to select one from a plurality of needle sizes and wherein the at least one threshold speed value is dependent on the selected needle size.

* * * * *